United States Patent [19]

Bucher et al.

[11] Patent Number: 4,872,919

[45] Date of Patent: Oct. 10, 1989

[54] METHOD FOR REMOVING PRECIPITATED CALCIUM CITRATE FROM JUICE PASTEURIZATION OR STERILIZATION EQUIPMENT

[75] Inventors: Michael S. Bucher, Wyoming; Paul J. Russo, Cincinnati, both of Ohio; Robert J. Schaar, Edgewood, Ky.

[73] Assignee: The Procter & Gamble Company, Cincinnati, Ohio

[21] Appl. No.: 149,465

[22] Filed: Jan. 28, 1988

[51] Int. Cl.$^4$ ............................................... B08B 3/08
[52] U.S. Cl. .......................................... 134/3; 134/28; 134/41
[58] Field of Search ................................ 134/3, 28, 31

[56] References Cited

U.S. PATENT DOCUMENTS

| | | | |
|---|---|---|---|
| 3,622,379 | 11/1971 | Fehmerling | 252/181 |
| 3,639,278 | 2/1972 | Hwa | 252/181 |
| 3,639,279 | 2/1972 | Gardner et al. | 252/181 |
| 4,357,254 | 11/1982 | Kapiloff et al. | 252/181 |
| 4,452,703 | 6/1984 | Ralston et al. | 210/698 |
| 4,496,470 | 1/1985 | Kapiloff et al. | 252/181 |

FOREIGN PATENT DOCUMENTS

| | | | |
|---|---|---|---|
| 675623 | 12/1963 | Canada | 134/3 |
| 0188975 | 7/1986 | European Pat. Off. | 134/3 |
| 2326447 | 12/1974 | Fed. Rep. of Germany | 134/3 |
| 7100481 | 4/1966 | Japan | 134/3 |
| 700774 | 2/1978 | U.S.S.R. | 134/3 |

Primary Examiner—Asok Pal
Attorney, Agent, or Firm—Eric W. Guttag; Chester Cekala; Richard C. Witte

[57] ABSTRACT

A method for removing precipitated calcium citrate which has deposited on the interior surface of juice pasteurization or sterilization equipment is disclosed. The interior surface of the juice pasteurization or sterilization equipment is contacted, at a temperature of at least about 150° F. (65.6° C.) with an aqueous acid solution containing an acid selected from acetic acid, fumaric acid, lactic acid, gluconic acid, adipic acid, citric acid, phosphoric acid, sulfuric acid, hydrochloric acid, nitric acid, malic acid and mixtures thereof to remove the deposited calcium citrate. The calcium citrate-laden solution is then removed from the juice pasteurization or sterilization equipment.

19 Claims, No Drawings

METHOD FOR REMOVING PRECIPITATED CALCIUM CITRATE FROM JUICE PASTEURIZATION OR STERILIZATION EQUIPMENT

TECHNICAL FIELD

This application relates to fruit juice beverages which are nutritionally supplemented with signifcant levels of calcium. This application particularly relates to a method for removing precipitated calcium citrate from pasteurization or sterilization equipment used in preparing these calcium-supplemented beverages.

Dietary calcium inadequacy may be a contributing cause to osteoporosis, at least for some populations. For example, a positive correlation between calcium intake and bone mass has been found across many age groups. It has also been suggested that the level of calcium intake early in life directly influences the peak bone mass achieved at skeletal maturity.

During the period of late teenage to young adulthood, it has been found that a significant reduction in dietary calcium intake typically occurs. This is especially true of the female population where reduced dietary calcium intake usually happens much earlier in life compared to their male counterparts. Accordingly, females, as a class, are especially susceptible to a prolonged calcium deficit over their life span. This calcium deficit may be one reason for the greater incidence of osteoporosis in postmenopausal women.

Calcium can be obtained from a variety of dietary sources. The primary sources of calcium are dairy products, in particular milk. Milk provides a very valuable source of dietary calcium. However, beginning in late teenage to young adulthood and continuing through later life, milk is typically not consumed in sufficient quantities by the general population to obtain needed levels of calcium. This may be caused by the unattractiveness of milk as a drink for "social occasions". Indeed, it has been found that teenage girls, and especially young adult women, generally find milk to be a socially unattractive drink, as well as too caloric and unappealing in taste. Additionally, a significant portion of the population becomes lactose intolerant as they reach maturity, resulting in gastrointestinal problems if they consume milk.

To achieve greater consumption of calcium, a more appealing alternative to milk is apparently needed. This alternative must be one which is consumed in sufficient quantities to provide nutritionally beneficial amounts of calcium. Beverages which are consumed often by the general public at breakfast are fruit juice products, especially orange juice. Like milk, orange juice has a wholesome, nutritional image. Also, orange juice is generally considered to have an appealing taste. Accordingly, orange juice nutritionally supplemented with calcium could be viewed as an additional vehicle for achieving greater dietary calcium intake throughout life.

Nutritional supplementation of orange juice, or other fruit juices, with significant levels of calcium is not straight forward. Milk contains, on average, about 0.12% calcium by weight. Inclusion of such a high level of calcium in orange juice requires consideration of a number of issues.

One potential issue is that the calcium, even when solubilized, can still precipitate out of the juice. Precipitation of calcium from juice concentrates can be a very significant problem because of the high level of calcium present. However, precipitation of calcium from single-strength juice products can also occur due to the acid systems and other components present in the juice. Orange juice naturally contains a mixture of citric acid and malic acid. The most thermodynamically stable calcium citrate species which form when a calcium source is added to orange juice are also the most insoluble. These insoluble calcium citrate species can precipitate out of the orange juice fairly rapidly.

Ready-to-serve, calcium-supplemented chilled juice products have presented special calcium precipitation problems. To prolong stability against microbial and mold growth, chilled juice products are pasteurized or sterilized prior to being packed. This typically involves passage of the juice stream through high temperature (typically from about 180° F. (82.2° C.) to about 212° F. (100° C.) or ultra-high temperature (typically from about 212° F. (100° C.) to about 260° F. (126.7° C.)) pasteurization or sterilization equipment. Examples of such equipment are plate and frame heat exchangers (high temperature) and direct steam infusion sterilizers (ultra-high temperature).

It has been surprisingly found that, as calcium containing fruit juice streams pass through high temperature pasteurization or sterilization equipment, calcium salts present in the juice stream precipitate out. This is particularly true of calcium-containing citrus juice streams involving calcium hydroxide or calcium carbonate as the source of calcium supplementation. When calcium-containing citrus juice streams pass through high temperature pasteurization or sterilization equipment, insoluble calcium citrate can precipitate out. This precipitated calcium citrate typically deposits on the interior equipment surface of the pasteurizer or sterilizer. This precipitated calcium citrate eventually flakes off into the finished chilled juice product stream. (In the case of plate and frame heat exchangers, the precipitated and deposited calcium citrate can additionally reduce heat transfer efficiency.)

This precipitation problem can be reduced, to a certain extent, by increasing the amount of acid, relative to the amount of calcium, in the juice stream. However, the resulting chilled juice product can have a very sour taste. Calcium salt precipitation can also be reduced by lowering the level of calcium included in the juice stream but with the obvious disadvantage of limiting process and product flexibility. Accordingly, the precipitation problems resulting from high temperature pasteurization or sterilization of calcium-containing juice streams need to be solved in a way which delivers the desired level of calcium, yet avoids greatly increasing the sourness of the finished chilled juice product.

BACKGROUND ART

U.S. Pat. No. 3,639,278 to Hwa, issued Feb. 1, 1972, relates to compositions for inhibiting and removing calcium and magnesium scales (e.g. carbonate, phosphate, sulfate and hydroxide scales) from heat transfer surfaces such as cooling water systems, cooling tower systems, industrial evaporators and boilers. (Hwa says that "because of their inverse solubility, these compounds [scales] tend to precipitate onto heat-exchange surfaces", see Col. 1, lines 32–34). These compositions comprise glycolic acid, and optionally but preferably, lignosulfonic acid or its respective water-soluble salt. See also U.S. Pat. No. 3,639,279 to Gardner et al, issued Feb. 1, 1972, which discloses removal of scale from subsurface and surface equipment used with oil and gas wells by an aqueous basic solution of diglycolic acid salts, salts of substituted acids of a diamine or tertiary amine such as EDTA, and a base such as ammonium, sodium or potassium hydroxide.

U.S. Pat. No. 4,357,254 to Kapiloff et al, issued Nov. 2, 1982, relates to a composition for cleaning fouled reverse osmosis membranes used in water purification systems. These membranes can become fouled with calcium and magnesium scales, as well as iron scales and organic fouling materials. The composition used to clean these membranes comprises a combination of monobasic sodium phosphate, dibasic sodium phosphate, citric acid, malic acid and a nonionic surfactant. Kapiloff et al specifically teach that malic and citric acid serve the dual function of dissolving calcium and magnesium scale, while preventing precipitation of phosphates caused by iron. See also U.S. Pat. No. 4,496,470 to Kapiloff et al, issued Jan. 29, 1985, discloses a similar cleaning composition based on monobasic sodium phosphate, dibasic sodium phosphate, at least one of citric, malic and sulfamic acid, and a nonionic detergent.

U.S. Pat. No. 4,452,703 to Ralston et al, issued June 5, 1984, relates to a method for preventing the formation of scale in sugar juice evaporation equipment. This is achieved by adding the sugar juice from 0.1 to 200 ppm of a polycarboxylic acid (or its salt) selected from polymaleic acid, amine adducts of maleic anhydride polymers, phosphonobutanetricarboxylic acid, phosphinocarboxylic acids and copolymers of acrylic acid and an hydroxylated lower alkyl acrylate.

U.S. Pat. No. 3,622,379 to Fehmerling, issued Nov. 23, 1971, relates to a method for treating shells from marine creates to remove material capable of sustaining microorganism growth and to produce a shiny natural appearing surface. In this method, the shells are contacted with an aqueous solution of 0.05 to 2.5% by weight of an acid capable of forming a substantially insoluble calcium salt upon the surface of the shell. These acids include phosphoric, citric, tartaric, malic, lactic, fluoric or fumaric acid. This acid solution is maintained at a temperature between 175° F. (79.4° C.) and 212° F. (100° C.) to react the acid with the calcium present in the shell so as to form a coating of insoluble calcium salt on the surface of the shell. The shell is then subjected to alkaline treatment with a solution of an alkaline salt, such as sodium carbonate or sodium bicarbonate, at a temperature between 175° F. (79.4° C.) and 212° F. (100° C.) to produce a relatively insoluble protective coating which is substantially impervious and continuous on the shell.

DISCLOSURE OF THE INVENTION

The present invention relates to a method for removing calcium citrate which has precipitated from a calciumcontaining fruit juice stream and which has deposited on the interior surface of the juice pasteurization or sterilization equipment. This method comprises the steps of:

(a) contacting the interior surface of the juice pasteurization or sterilization equipment, at a temperature of at least about 150° F. (65.6° C.), with an aqueous acid solution having a pH of from about 0 to about 4.5 and containing from about 0.5 to about 20% by weight of an acid selected from acetic acid, fumaric acid, lactic acid, gluconic acid, adipic acid, citric acid, phosphoric acid, sulfuric acid, hydrochloric acid, nitric acid, malic acid and mixtures thereof to remove precipitated calcium citrate deposited on the interior surface; and (b) removing the calcium citrate-laden solution from the equipment.

The method of the present invention solves the calcium salt, and in particular calcium citrate, precipitation problems caused by high temperature pasteurization or sterilization of calcium-containing fruit juice streams, and especially calcium-containing citrus juice streams. This method can reduce the time required for periodic cleaning of pasteurization or sterilization equipment through which calcium-containing juice streams pass, while at the same time maintaining the sterility of the pasteurized or sterilized juice stream.

A. Definitions

As used herein, the term "fruit juice beverage" refers to a fruit juice product which comprises at least about 45% fruit juice and which is in a single-strength, ready-to-serve, drinkable form. Fruit juice beverages of the present application can be of the "full-strength" type which typically comprises at least 95% fruit juice.

Fruit juice beverages within the scope of the present application also include extended juice products which are referred to as "nectars." These extended juice products typically comprise from about 50 to about 90% fruit juice. Preferred extended juice products comprise from about 50 to about 70% fruit juice.

As used herein, the term "concentrated fruit juice" refers to fruit juice from which a portion of the water has been removed.

As used herein, the term "fruit juice stream" refers to a generally homogeneous mixture of fruit juice materials, including concentrated fruit juice, fruit juice aroma and flavor volatiles, peel oils, sensible pulp or pomace, plus other materials such as additional edible acids, sources of calcium, other minerals, vitamins, and the like.

As used herein, the term "fruit juice" refers to citrus juices, noncitrus juices such as apple juice, grape juice, pear juice, cherry juice, berry juice, pineapple juice, peach juice, apricot juice, plum juice, prune juice, passion fruit juice, banana juice, and mixtures of these juices.

As used herein, the term "citrus juice" refers to fruit juices selected from orange juice, lemon juice, lime juice, grapefruit juice, trangerine juice and mixtures thereof.

All amounts of fruit juice referred to herein are on a single-strength basis.

As used herein, the term "comprising" means various components can be conjointly employed in the fruit juice beverages and fruit juice streams of the present application. Accordingly, the term "comprising" encompasses the more restrictive terms "consisting essentially of" and "consisting of."

As used herein, the terms "pasteurize" and "pasteurization" refer to treatment processes where materials are heated, without radiation, to temperatures and for periods of time sufficient to at least partially sterilize the material against microbial and mold growth, without substantial alteration of the chemical composition of the material. Pasteurized materials are characterized by prolonged stability against spoilage by microbial and mold growth. The terms "pasteurize" and "pasteurization" include the more restrictive terms "sterilize" and "sterilization" where the treated material is substantially free of microbial and mold growth.

B. Preparation of Calcium-Containing Fruit Juice Streams

The calcium-containing fruit juice streams described in the present application are typically prepared by what is referred to as a premix method. See U.S. application Ser. No. 860,607 to David C. Heckert, filed May 7, 1986 (herein incorporated by reference), which discloses this premix method. The following discussion of this method will generally be with regard to formation of calcium-containing orange juice streams, which are highly preferred fruit juice streams according to the present application. However, with appropriate modification, this premix method can also be used to prepare calcium-containing fruit juice streams based on other citrus juices such as grapefruit juice, noncitrus juices such as apple juice, as well as mixtures of juices.

In this premix method, an acid component comprising citric acid and malic acid is typically dissolved in the appropriate quantity of water. (If desired, fruit juice or concentrated fruit juice such as lemon juice can be used to supply a portion of the acids). Generally, this acid component comprises from 0 to 100% by weight citric acid and from 0 to 100% by weight malic acid. For orange juice streams, this acid component typically comprises from about 5 to about 90% by weight citric acid and from about 10 to about 95% by weight malic acid, and preferably comprises from about 5 to about 60% by weight citric acid and from about 40 to about 95% by weight malic acid. (For noncitrus juice streams such as apple juice streams, this acid component typically comprises from about 5 to 100% by weight citric acid and from 0 to about 95% by weight malic acid, and preferably comprises from about 20 to 100% by weight citric acid and from 0 to about 80% by weight malic acid.) As a rule, the ratio of these acids is selected to provide optimum flavor character in the juice stream. These acids can be added in their undisassociated form or else as the respective sour salt, i.e., citrate, malate.

Once the solution containing the dissolved acids is formed, a source of calcium is then added. Calcium hydroxide, calcium oxide or calcium carbonate are particularly suitable sources of calcium. The weight ratio of dissolved acids to calcium in the solution is typically from about 0.5 to about 12. Preferably, this weight ratio is from about 1 to about 6.

Addition of calcium carbonate, calcium oxide, or calcium hydroxide to the aqueous solution of acids provides a premix containing an at least meta-stable solution of solubilized calcium. This is due to the fact that highly soluble calcium citrate and malate species such as CaHcitrate, Ca(H$_2$ citrate)$_2$, and CaHmalate are formed in the solution due to the reaction between the calcium source and the acids. Without added stabilizers, the highly soluble calcium citrate species are stable in the premix solution for periods up to only about a few hours. After this short period of time, the highly soluble citrate species tend to disproportionate to the corresponding acid and the more thermodynamically stable, insoluble calcium citrate salts, such as Ca$_3$ citrate$_2$.

To improve the stability of the calcium malate and especially citrate species in the premix solution, it is preferred to include a premix stabilizer. Materials which can complex with calcium and/or act as crystallization inhibitors are useful as premix stabilizers. These materials include sugars, such as sucrose, glucose, fructose, high fructose corn syrup, invert sugar, and polysaccharides such as pectin, algins, hydrolyzed starches, xanthan gum, and other edible gums. Concentrated juices which naturally contain both sugars and polysaccharides are particularly suitable premix stabilizers. Preferred premix stabilizers are sucrose and high fructose corn syrup (especially for extended juice products) and concentrated orange juice having a sugar content of from about 35 to about 80° Brix whose source is described hereafter.

The premix stabilizer can be added immediately after the calcium source is added to the aqueous solution containing the acids. (When calcium carbonate is the calcium source, carbon dioxide evolution is preferably allowed to substantially cease before the premix stabilizer is added). However, if desired, the premix stabilizer (especially in the case of sugars and concentrated juice) can be added to the aqueous solution of the acids prior to addition of the calcium source. The amount of premix stabilizer included in the premix solution typically depends upon the stabilizer used. When sugars are used as the premix stabilizer, they are typically added in an amount sufficient to provide a sugar content of from about 2° to about 40° Brix. When polysaccharides are used, the amount can vary widely, but is typically from about 0.01 to about 0.5% on a weight/volume basis. When concentrated juice is used as the premix stabilizer, it is typically included in an amount sufficient to provide a sugar content of from about 2° to about 12° Brix (preferably from about 2° to about 6° Brix).

The premix solution of solubilized calcium is typically prepared in a batch-type fashion, as in the description above, at room temperature. However, this premix solution can also be prepared in a continuous fashion. In this continuous method, the ingredients (water, acids, calcium source and optional premix stabilizer) are constantly metered together to form the premix solution. The level at which the ingredients are metered is adjusted, as necessary, to insure appropriate solubilization of the calcium in the premix solution and to provide the appropriate acidity.

The premix solution containing the solubilized calcium is combined in a mix tank with chilled (e.g., below about 40° F. (4.4° C.)) concentrated orange juice having a sugar content of from about 35° to about 80° Brix (preferably from about 60 to about 70° Brix.), orange juice aroma and flavor volatiles, plus other orange juice materials such as pulp and peel oils, to provide the calcium-containing orange juice stream. The particular proportions of premix solution, concentrated juice, aroma and flavor volatiles, pulp and peel oil used will depend upon a number of different factors, including the degree of calcium supplementation desired and the type of orange juice beverage involved (full-strength juice beverage or extended juice beverage).

The concentrated orange juice, orange juice aroma and flavor volatiles, sensible pulp and peel oils used in preparing clacium-containing orange juice streams of the present application can be obtained from standard orange juice processing. See Nagy et al., *Citrus Science and Technology*, Vol. 2, (AVI Publishing Co. 1977), pp. 177–252 (herein incorporated by reference) for standard processing of oranges, grapefruit and tangerines. See also Nelson et al, *Fruit & Vegetable Juice Processing Technology* (3rd Ed., AVI Publishing 1980), pp. 180–505 (herein incorporated by reference) for standard processing of noncitrus juices such as apple juice, grape juice, pineapple juice, etc. to provide sources of juices and other juice materials for noncitrus juice streams. Juices from different oranges (e.g., Florida Valencia, Parson Brown, Hamlin, Pineapple, Brazilian Valencia, Per Rio) are frequently blended to adjust the sugar to acid ratio. A sugar to acid ratio of from about 8:1 to about 20:1 is considered acceptable. However, preferred sugar to acid ratios are typically from about 12:1 to about 18:1.

The peel of the orange can be initially rasped to provide peel oils which can be used in the orange juice stream of the present application. Juice is typically extracted from the oranges by using automatic juicing machines, or less often by hand squeezing of the oranges. The type of equipment used to extract the juice is not critical. The raw juice exiting from the squeezing device contains sensible pulp, rag and seeds. The rag and seed are separated from the juice and sensible pulp in a primary finishing step. The sensible pulp is then typically separated from the remaining feed juice in a secondary finishing step. (This separated sensible pulp can be used as a source of sensible pulp in the orange juice streams of the present application.)

In order to preserve the more desirable orange aroma and flavor compounds present, the free juice can be stripped with steam to remove orange aroma and flavor volatiles. These volatiles are then recovered in the form of an orange aroma/flavor condensate which is separated to provide aqueous orange stripper essence and orange stripper oil. See European patent application 110,638 to Powers et al, published June 13, 1984 (herein incorporated by reference) which discloses a suitable volatile stripping/recovery process, and the resulting stripper essence and stripper oil materials obtained. Other sources of aroma/flavor materials can also be used, in whole or in part. For example, commercial orange essences, commercial orange oils and cold pressed peel oils can be used to supply a portion, or all, of the aroma/flavor materials present in the orange juice stream. Non-orange sources of natural flavoring can also be used as sources of aroma/flavor materials.

The feed juice (stripped or unstripped) can be concentrated by a variety of techniques which typically include evaporative concentration or freeze concentration. In evaporative concentration, the feed juice is passed through an evaporator, or more typically, a series of evaporators. Examples of suitable evaporators include the falling film type or, more typically, temperature accelerated short time evaporators (TASTE). Most concentrated orange juices are obtained by evaporative concentration. However, freeze concentration can also be used to obtain concentrated orange juice useful in the orange juice stream of the present invention. Freeze concentration typically involves passing the serum portion of the feed juice through a scraped wall heat exchanger to form substantially pure ice crystals which are then separated from the concentrated juice. A preferred freeze concentration method is disclosed in U.S. Pat. No. 4,374,865 to Strobel, issued February 22, 1983, which is incorporated by reference. Unlike evaporative concentration, concentrated orange juice obtained by freeze concentration typically contains the aroma and flavor volatiles as well.

The calcium-containing fruit juice streams of the present application contain the sugars normally present in fruit juice products. These sugars include sucrose, fructose, high fructose corn syrup, glucose, invert sugar, and mixtures thereof. The amount of sugar naturally present in the fruit juice is usually sufficient for the fruit juice streams of the present application. However, in the case of extended fruit juice beverages, sugar is typically added, usually in the form of sucrose or high fructose corn syrup.

In addition to sugar, calcium-containing fruit juice streams used to prepare extended fruit juice beverages can contain other sweeteners. Outer suitable sweeteners include saccharin, cyclamates, acetosulfam, L-aspartyl-L-phenylalanine lower alkyl ester sweeteners (e.g. aspartame), L-aspartyl-D-alanine amides disclosed in U.S. Pat. No. 4,411,925 to Brennan et al, issued Oct. 23, 1983 (herein incorporated by reference), L-aspartyl-D-serine amides disclosed in U.S. Pat. No. 4,399,163 to Brennan et al, issued Aug. 16, 1983 (herein incorporated by reference), L-aspartyl-L-1-hydroxymethylalkaneamide sweeteners disclosed in U.S. Pat. No. 4,338,346 to Brand, issued Dec. 21, 1982 (herein incorporated by reference), L-aspartyl-1-hydroxyethylalkaneamide sweeteners disclosed in U.S. Pat. No. 4,423,029 to Rizzi, issued Dec. 27, 1983 (herein incorporated by reference), L-aspartyl-D-phenylglycine ester and amide sweeteners disclosed in U.S. Pat. No. 4,692,512 to Janusz, issued Sept. 8, 1987 (herein incorporated by reference), L-aspartyl-D-heteroaromatic-substituted-glycine ester and amide sweeteners disclosed in U.S. Pat. No. 4,692,513 to Blum et al, issued September 8, 1987 (herein incorporated by reference), and the like. A particularly preferred sweetener for use in such extended juice products is aspartame.

The solids content (primarily as sugar solids) of the resulting calcium-containing fruit juice stream can range from about 5° to about 25° Brix. Typically, the solids content of such juice streams depends upon the amount of fruit juice contained therein. For calcium-containing fruit juice streams used to prepare full-strength beverages containing at least about 95% fruit juice, the solids content is typically from about 9° to about 16° Brix. For fruit juice streams used to prepare extended juice beverages which comprise from about 50 to about 90% fruit juice, the solids content is typically from about 8° to about 14° Brix (no other sweetener besides sugar) or from about 5° to about 9° Brix (other sweetener containing).

The level of solubilized calcium (i.e., calcium ion dissolved or suspended) present in the fruit juice stream usually depends on the degree of calcium supplementation desired. Generally, these fruit juice streams contain significant levels of solubilized calcium. The calcium containing fruit juice streams of the present application generally contain from about 0.05 to about 0.26% by weight solubilized calcium. Typically fruit juice streams contain from about 0.10 to about 0.20% by weight solubilized calcium.

The calcium-containing fruit juice streams of the present application usually contain significant levels of citric acid (added citric acid, plus that naturally present in the fruit juice). For citrus juice streams, the total level of citric acid, (i.e., added, plus that naturally present) can range from about 0.4 to about 4% by weight, and is preferably from about 0.6 to about 2.5% by weight. For noncitrus fruit (e.g., apple) juice streams, the total level of citric acid preferably ranges from 0.4 to about 2.5% by weight.

C. Pasteurization of Calcium-Containing Fruit Juice Stream

After it is formulated, the calcium-containing fruit juice stream is then subjected to a pasteurization or sterilization step. Most fruit juice beverages prepared from these juice streams are packaged as chilled juice products. Unless the juice stream is prepared aseptically, a pasteurization or sterilization step is required to prolong the stability of the chilled juice product against microbial and mold growth.

Pasteurization of chilled juice products can be achieved by passage of the juice stream through high temperature pasteurization equipment. High temperature processing typically refers to processing at temperatures of from about 180° to about 212° F. (from about 82.2° to about 100° C.). Pasteurization of fruit juice streams by high temperature processing can be carried out through the use of indirect heat exchangers. Indirect heat exchangers can be either of the shell and tube type, or, more typically, of the plate and frame type. In either case, pasteurization of fruit juice streams with indirect heat exchangers tends to result in chilled juice products having poorer quality. This is due to the fact that the juice stream is exposed to high surface temperatures for relatively long periods of time because of inefficient heat transfer.

The calcium-containing fruit juice streams of the present application are preferably pasteurized or sterilized by the use of ultra-high temperature processing. Ultra-high temperature processing typically refers to processing at temperatures of from about 212° to about 260° F. (from about 100° to about 126.7° C.). The advantage of ultra-high temperature processing is that the rate of microbe kill and inactivation increases faster than the rate of chemical degradation of the juice stream. Accordingly, by the use of ultra-high temperature processing, it is possible to pasteurize or sterilize fruit juice streams without significantly and adversely affecting the quality of the resulting chilled juice product.

Ultra-high temperature processing is typically carried out by direct heat exchange methods. Direct heat exchange methods are capable of reducing the length of time the juice stream is exposed to very high temperatures to as little as a few seconds, e.g., from about 2 to about 6 seconds. Direct heat exchange methods include both steam injection and steam infusion. Direct steam infusion methods are particularly preferred for pasteurizing or sterilizing calcium-containing fruit juice streams of the present application. Examples of suitable direct steam infusion pasteurization and sterilization systems include the Crepaco Ultra-Therm infusion heater, as well as direct steam infusion systems supplied by CherryBurrell and DASI.

In direct steam infusion pasteurization or sterilization, the juice stream falls as thin films or sheets through a pressurized steam atmosphere. The steam condenses within the juice stream, causing it to be instantaneously heated by the release of the latent heat from the steam. Simultaneously, the stream is diluted with an amount of water directly related to the desired temperature rise. Fruit juice aroma and flavor materials volatilized during this direct steam infusion process are subsequently recondensed back into the fruit juice stream.

The fuit juice stream is preferably passed through a preheater prior to direct steam infusion pasteurization or sterilization. Typically, the fruit juice stream is preheated to a temperature of from about 40° to about 100° F. (from about 4.4° to about 37.8° C.). Preferably, the fruit juice stream is preheated to a temperature from about 60° to about 85° F. (from about 15.6° to about 29.4° C.). Preheating of the fruit juice stream minimizes the time and temperature necessary to achieve pasteurization or sterilization during direct steam infusion heating. Reducing the time and temperature of pasteurization or sterilization better preserves the quality of the resulting chilled juice products.

Once pasteurized or sterilized by direct steam infusion heating, the fruit juice stream, plus any resulting fruit juice aroma and flavor volatiles, are typically condensed and cooled by a bank of heat exchangers typically referred to as chillers. This cooling system is closed so that any vapors, including water vapors and aroma/flavor volatiles, are recondensed back within the fruit juice stream. The final temperature of the pasteurized or sterilized fruit juice stream after cooling is typically from about 30° to about 50° F. (from about −1.1° to about 10° C.). Preferably, the pasteurized fruit juice stream is cooled to a temperature of from about 30° to about 40° F. (from about −1.1° to about 4.4° C.).

D. Removal of Precipitated Calcium Citrate by Acid Solution

The calcium-containing fruit juice streams of the present application contain significant levels of solubilized calcium, as well as significant levels of citric acid. Generally, these calcium-containing fruit juice streams are fairly stable against precipitation of calcium citrate at temperatures below those used for pasteurization or sterilization. However, it has been surprisingly found that the calcium citrate present in these juice streams precipitates out at the high temperatures required for pasteurization or sterilization. This precipitated calcium citrate deposits itself on the interior equipment surface of the pasteurizer or sterilizer, and eventually flakes off into the finished juice product stream. In the case of plate and frame heat exchangers used for high temperature pasteurization, the precipitated and deposited calcium citrate can additionally reduce heat transfer efficiency.

The propensity of calcium citrate to precipitate out and deposit during pasteurization or sterilization of the calcium-containing fruit juice stream is related to several factors. These factors include the level of solubilized calcium, the level of citric acid and the particular fruit juice stream involved. This can be best understood by reference to the following table which shows the volumes of orange and grapefruit juice streams which can be pasteurized in a direct steam infusion heater before calcium citrate precipitation becomes a significant problem.:

| Type of Stream | Level of Calcium (%) | Level of Citric Acid (%) | Juice Stream pH | Volume (gallons) Which can be Pasteurized |
|---|---|---|---|---|
| 100% orange juice | 0.12 | 1.1 | 4.2 | 12000 |
| 100% orange juice | 0.18 | 1.1 | 4.3 | 2000 |
| 60% grapefruit juice | 0.12 | 1.0 | 3.8 | 16000 |
| 60% grapefruit juice | 0.18 | 0.9 | 3.9 | 8000 |

Periodically, the calcium citrate which has precipitated from these calcium-containing fruit juice streams and deposited on the interior surface of the pasteurization or sterilization equipment needs to be removed. In the method of the present invention, this is achieved by contacting the interior surface of the equipment with an aqueous solution of an acid. Suitable acids include acetic acid, fumaric acid, lactic acid, gluconic acid, adipic acid, citric acid, phosphoric acid, sulfuric acid, hydrochloric acid, nitric acid, malic acid and mixtures of these acids. Aqueous acid solutions of phosphoric acid, citric acid and especially malic acid are considered to be particularly preferred due to their ability to remove precipitated calcium citrate.

In formulating the aqueous acid solution, the critical factors are the pH of the solution and the concentration of acid contained therein. The pH of the aqueous acid solution can range from about 0 to about 4.5, while the concentration of acid can range from about 0.5 to about 20% by weight. Preferably, the aqueous acid solution has a pH of from about 1 to about 3.5, while the concentration of acid is from about 1 to about 10% by weight. The aqueous acid solution can be formulated to have the desired pH and concentration, or else can be formulated by diluting, with water, a more concentrated stock solution of the acid.

Whenever it is desired to remove any precipitated calcium citrate, passage of the calcium-containing fruit juice stream is discontinued to the pasteurization or sterilization equipment. If desired, a water stream can be passed through the pasteurization or sterilization equipment to remove any residual juice stream. The aqueous acid solution is then passed through this pasteurization or sterilization equipment for a period of time sufficient to remove any precipitated calcium citrate which has deposited on the interior surface of the equipment. Typically, contacting the interior surface of the pasteurization or sterilization equipment for a period of at least about 5 minutes is sufficient to remove any precipitated calcium citrate which has been deposited. Preferably, the aqueous acid solution contacts the interior surface of the pasteurization or sterilization equipment for a period of from about 5 to about 20 minutes. The flow rate of the aqueous acid solution through the equipment should be such that the solution does not become overly saturated with calcium cirate. Higher flow rates are preferred from the standpoint of avoiding calcium citrate saturation.

In addition, it has been found important to have the aqueous acid solution contact the interior surface of the pasteurization or sterilization equipment at a temperature of at least about 150° F. (65.6° C.). At temperatures much below about 150° F. (65.6° C.), the ability of the aqueous acid solution to dissolve the precipitated calcium citrate is greatly diminished. Preferably, the aqueous acid solution contacts the interior surface of the equipment at the temperatures required to pasteurize or sterilize the calcium-containing fruit juice stream, i.e. from about 180° to about 260° F. (from about 82.2° to about 126.7° C.). Most preferably, the aqueous acid solution contacts the interior surface of the equipment at a temperature from about 212° to about 260° F. (from about 100° to about 126.7° C.).

After passage of the aqueous acid solution through the pasteurization or sterilization equipment, the resulting calcium citrate-laden solution is then removed. If desired, this calcium citrate-laden solution can be discarded, typically after appropriate neutralization with a base such as sodium or potassium hydroxide. However, this calcium citrate-laden solution can usually be recycled through the pasteurization or sterilization equipment to remove additional precipitated and deposited calcium citrate. Typically, additional acid is added before this calcium-laden solution is recycled. Once the recycled solution of acid becomes saturatd with calcium citrate, it is then discarded, preferably after it has been neutralized with an appropriate base such as sodium or potassium hydroxide.

Once the calcium citrate-laden solution is removed, passage of more calcium-containing fruit juice stream through the pasteurization or sterilization equipment can be continued until it is again necessary to remove precipitated calcium citrate. If desired, a water stream can be passed through the pasteurization or sterilization equipment before passage of the juice stream to remove the residual aqueous acid solution.

Specific Embodiments of the Method for Removing Precipitated Calcium Citrate from a Direct Stream Infusion Heater According to the Present Invention.

The following are specific embodiments of the method for removing precipitated calcium citrate from a direct steam infusion heater in accordance with the present invention:

Embodiment 1

A calcium-containing orange juice stream was formulated from the following ingredients:

| Ingredient | Wt. % |
| --- | --- |
| Orange concentrate (65° Brix) | 20.8 |
| Orange pulp | 2.6 |
| Malic acid | 0.56 |
| Citric acid | 0.03 |
| Calcium hydroxide | 0.31 |
| Water-soluble flavors | 0.16 |
| Oil-soluble flavors | 0.0007 |
| Water | Balance |

This juice stream (solids content of approximately 14.2° Brix) was sterilized by passage through a Crepaco Ultra-Therm Infusion Heater at a temperature of at least 215° F. (101.7° C.) with a residence time of at least 2.5 seconds. After 2000 gallons (7570 liters) of juice stream had been sterilized, sufficient calcium citrate had precipitated out and deposited on the interior surface of the infusion heater to require removal. An aqueous solution of 4% by weight malic acid (pH about 2) was then passed through the infusion heater at a temperature of at least 215° F. (101.7° C.) with a residence time of at least 2.5 seconds, i.e. those conditions required for sterilization of the juice stream. After 20 minutes of treatment with the malic acid solution, the infusion heater was inspected for precipitated calcium citrate. None was found.

Embodiment 2

A calcium-containing grapefruit juice stream was formulated from the following ingredients:

| Ingredient | Wt. % |
| --- | --- |
| Grapefruit concentrate (62° Brix) | 11.5 |
| Grapefruit pulp | 1.7 |
| Malic acid | 0.40 |
| Citric acid | 0.26 |
| Calcium hydroxide | 0.27 |
| Oil-soluble flavors | 0.013 |
| Liquid sucrose (67.5° Brix) | 6.9 |
| Ascorbic acid | 0.02 |
| Water | Balance |

This juice stream (solids content of approximately 12.5° Brix) was sterilized by passage through a Crepaco Ultra-Therm Infusion Heater at a temperature of at least 215° F. (101.7° C.) with a residence time of at least 2.5 seconds. After 16,000 gallons (60,560 liters) of juice stream had been sterilized, passage of the juice stream to the infusion heater was discontinued. An aqueous solution of 4% by weight malic acid (pH about 2) was then passed through the infusion heater at a temperature of at least 215° F. (101.7° C.) with a residence time of at least 2.5 seconds. After 5 minutes of treatment with the malic acid solution, the infusion heater was ready for sterilization of more of the calcium-containing grapefruit juice stream.

Embodiment 3

A calcium-containing orange juice stream was formulated from the following ingredients:

| Ingredient | Wt. % |
| --- | --- |
| Orange concentrate (65° Brix) | 20.8 |
| Orange pulp | 2.6 |
| Malic acid | 0.51 |
| Citric acid | 0.03 |
| Calcium hydroxide | 0.37 |
| Water-soluble flavors | 0.20 |
| Oil-soluble flavors | 0.006 |
| Water | Balance |

This juice stream (solids content of approximately 14.4° Brix) was sterilized by passage through a Crepaco Ultra-Therm Infusion heater at a temperature of at least 215° F. (101.7° C.) with a residence time of at least 2.5 seconds. Sterilization was continued until flakes of calcium citrate were seen in the juice stream exiting the infusion heater. An inspection revealed a coating of calcium citrate on the interior surface of the infusion heater. An aqueous solution of 4% by weight citric acid (pH about 2) was then passed through the infusion heater at a temperature of at least 215° F. (101.7° C.) with a residence time of at leat 2.5 seconds. After 15 minutes of treatment with the citric acid solution, the interior surface of the infusion heater was again inspected for precipitated calcium citrate. None was found.

What is claimed is:

1. A method for removing calcium citrate which has precipitated from a calcium-containing fruit juice stream and which has deposited on the interior surface of juice pasteurization or sterilization equipment, said method comprising the steps of:
   (a) contacting the interior surface of the juice pasteurization or sterilization equipment, at a temperature of at least about 150° F. (65.6° C.), with an aqueous acid solution having a pH of from about 0 to about 4.5 and containing from about 0.5 to about 20% by weight of an acid selected from the group consisting of acetic acid, fumaric acid, lactic acid, gluconic acid, adipic acid, citric acid, phosphoric acid, sulfuric acid, hydrochloric acid, nitric acid, malic acid and mixtures thereof to remove precipitated calcium citrate deposited on the interior surface; and
   (b) removing the calcium citrate-laden solution from the equipment.

2. The method of claim 1 wherein the interior surface is contacted with the aqueous acid solution for at least about 5 minutes during step (a).

3. The method of claim 2 wherein the interior surface is contacted with the aqueous acid solution for from about 5 to about 20 minutes during step (a).

4. The method of claim 2 wherein the aqueous acid solution has a pH of from about 1 to about 3.5 and comprises from about 1 to about 10% by weight acid.

5. The method of claim 4 wherein the acid is selected from the group consisting of phosphoric acid, citric acid and malic acid.

6. The method of claim 5 wherein the acid is malic acid.

7. The method of claim 2 wherein the interior surface is contacted with the aqueous acid solution at a temperature of from about 180° to about 260° F. (from about 82.2° to about 126.7° C.) during step (a).

8. The method of claim 7 wherein the interior surface is contacted with the aqueous acid solution at a temperature of from about 212° to about 260° F. (from about 100° to about 126.7° C.) during step (a).

9. The method of claim 8 wherein the equipment is a direct stream infusion heater.

10. The method of claim 2 wherein the deposited calcium citrate precipitated from a calcium-containing citrus juice stream.

11. The method of claim 10 wherein the calciumcontaining citrus juice stream is a calcium-containing orange juice stream.

12. The method of claim 1 wherein said contacting step comprises flowing the aqueous acid solution through the equipment.

13. A method for removing calcium citrate which has precipitated from a calcium-containing citrus juice stream and which has deposited on the interior surface of juice pasteurization or sterilization equipment, said method comprising the steps of:
   (a) flowing an aqueous acid solution having a pH of from about 1 to about 3.5 and containing from about 1 to about 10% by weight of an acid selected from the group consisting of phosphoric acid, citric acid and malic acid through the juice pasteurization or sterilization equipment, so as to contact the interior surface thereof with the aqueous acid solution at a temperature of from about 180° to about 260° F. (from about 82.2° to about 126.7° C.) for at least about 5 minutes and so as to remove precipitated calcium citrate deposited thereon; and
   (b) removing the calcium citrate-laden solution from the equipment.

14. The method of claim 13 wherein the acid is malic acid.

15. The method of claim 13 wherein the acid is citric acid.

16. The method of claim 13 wherein the interior surface is contacted with the aqueous acid solution for from about 5 to about 20 minutes during step (a).

17. The method of claim 16 wherein the interior surface is contacted with the aqueous acid solution at a temperature of from about 212° to about 260° F. (from 100° to about 126.7° C.) during step (a).

18. The method of claim 17 wherein the equipment is a direct steam infusion heater.

19. The method of claim 13 wherein the deposited calcium citrate precipitated from a calcium-containing orange juice stream.

* * * * *